United States Patent [19]

Rühl et al.

[11] Patent Number: 5,808,160

[45] Date of Patent: Sep. 15, 1998

[54] PREPARATION OF HYDROXY-ALKYL-SUBSTITUTED AMINOALKYNES WITH HETEROGENOUS CATALYSIS

[75] Inventors: Thomas Rühl, Frankenthal; Thomas Preiss, Ludwigshafen; Jochem Henkelmann, Mannheim, all of Germany

[73] Assignee: BASF Aktiengesellschaft, Ludwigshafen, Germany

[21] Appl. No.: 847,486

[22] Filed: Apr. 25, 1997

[30] Foreign Application Priority Data

May 3, 1996 [DE] Germany .................. 196 17 802.9

[51] Int. Cl.⁶ .................................................. C07C 213/00
[52] U.S. Cl. .................... 564/503; 544/335; 544/401; 546/248; 564/355; 564/360; 564/383; 564/471; 564/472; 564/473; 564/485; 564/506
[58] Field of Search ..................... 544/335, 401; 546/248; 564/355, 360, 383, 471, 472, 473, 485, 503, 506

[56] References Cited

U.S. PATENT DOCUMENTS 3,496,232  2/1970  Tedeschi et al. .................. 260/583

4,148,824  4/1979  Hoffmann et al. .................. 260/585

FOREIGN PATENT DOCUMENTS 080 794  6/1983  European Pat. Off. .

OTHER PUBLICATIONS

Libman et al., *J. of Gen. Chem. USSR,* vol. 31, 1961, pp. 2127–2132.

*Chem. Abst.,* vol. 66, No. 25, Jun. 19, 1967, Abs. No. 115346, Volkov et al., "Synthesis and reactions of tertiary diacetylene— and alkoxyenynyl alicyclic alcohols".

*Primary Examiner*—Peter O'Sullivan
*Attorney, Agent, or Firm*—Keil & Weinkauf

[57] ABSTRACT

Hydroxyalkyl-substituted aminoalkynes of the general formula I

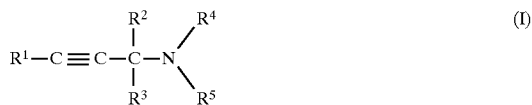

where at least one of the substituents $R^1$, $R^4$ or $R^5$ is hydroxyalkyl are prepared in a reaction with heterogeneous catalysis.

14 Claims, No Drawings

PREPARATION OF HYDROXY-ALKYL-SUBSTITUTED AMINOALKYNES WITH HETEROGENOUS CATALYSIS

The present invention relates to a process for preparing aminoalkynes which have at least one hydroxyalkyl substituent.

The preparation of aminoalkynes without hydroxyalkyl substituents has been known for a long time and is used industrially. This generally entails subjecting appropriately substituted alkynes, carbonyl compounds and amines to a Mannich condensation with homogeneous or heterogeneous catalysis.

Processes of this type with homogeneous catalysis are widely used and extensively described. Thus, for example, CH-A-669 192 describes the preparation of pharmacologically active N-arylalkyl-substituted aminoalkynes in a reaction with homogeneous catalysis by copper and zinc salts such as CuCl or $ZnCl_2$.

U.S. Pat. No. 3,496,232 describes, for example, the preparation of N-alkyl-substituted aminoalkynes in a Mannich reaction with homogeneous or heterogeneous catalysis by salts of metals of the first or second subgroup, e.g. the chlorides, acetates, formates and acetylides and, specifically copper acetylide, which in the case of the variant with heterogeneous catalysis are used on an inert carrier.

EP-A-0 080 794 describes a process for preparing N,N-disubstituted propynylamines with heterogeneous catalysis by, preferably, copper acetylides on a magnesium silicate carrier doped with bismuth oxide. The reaction is carried out, for example, in a stirred reactor with a suspended catalyst or in a fixed bed, with acetylene pressures of about 0.1 to 20 atm occurring.

In none of the publications discussed above does the skilled worker find any hint that hydroxyalkyl-substituted aminoalkynes could be prepared from alkyne, amine and carbonyl compound components.

DE-A-26 37 425 describes the preparation of dialkylamino-2-alkyn-4-ols by reacting formaldehyde, dialkylamine and an alkynol. However, in order to obtain satisfactory yields, it is necessary to comply with specific process conditions: it is necessary to work in acidic solution, preferably at pH 5, using a specific catalyst system, namely a combination of bromides soluble in the reaction mixture, iodides or iodine and soluble Cu(II) compounds. There is no suggestion that the reaction could be carried out with heterogeneous catalysis in the neutral or alkaline pH range. Nor does this publication contain any hint that N-hydroxyalkyl-substituted aminoalkynes can be prepared.

The skilled worker is aware that, when preparing aminoalkynes with hydroxyalkyl substituents on the nitrogen atom and/or on the alkyne carbon atom, a whole range of side reactions is to be expected on reaction of a mixture of carbonyl compound, alkyne and amine, which are hydroxyalkyl-substituted where appropriate. When mono- or dihydroxyalkyl-substituted amines and a carbonyl compound are used, ring closure reactions must be expected, such as oxazolidine formation. This particularly applies when β-amino alcohols are used as amine component, and when alkaline reaction conditions are employed in anhydrous solvents or in the presence of dehydrating agents, and not, as described in DE-A-26 37 425, in acidic aqueous solution. In addition, the formation of acetals from the hydroxyalkyl-substituted reactants and the carbonyl compound must be expected. These acetals have increased stability under alkaline reaction conditions. Furthermore, there may also be formation of open-chain products of condensation of a hydroxyalkyl-substituted alkyne, the amine component and an appropriate aldehyde. The risk of a side reaction is particularly great when the three reactants, amine, alkyne and carbonyl compound, are employed simultaneously.

It is an object of the present invention to provide a process for preparing hydroxyalkyl-substituted aminoalkynes which leads to high yields of the required products and needs no special measures for adjusting the pH.

We have found that this object is achieved by a process in which an alkyne is reacted with a carbonyl compound and an amine with heterogeneous catalysis, where at least one of the substituents on the amine nitrogen or on the non-aminoalkylated alkyne carbon is a hydroxyalkyl substituent. We have also found that no special measures are needed to adjust the pH; this is because the neutral to alkaline pH range which is predetermined by the reactants can be used without the expected unwanted side reactions occurring.

The present invention relates to a process for preparing hydroxyalkyl-substituted aminoalkynes of the general formula I

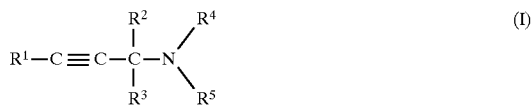

where
$R^1$ is hydrogen, alkyl, haloalkyl, cycloalkyl, aryl, alkoxy, alkoxyalkyl or hydroxyalkyl;
$R^2$ and $R^3$ are, independently of one another, hydrogen, alkyl, haloalkyl, aryl or alkoxy;
$R^4$ and $R^5$ are, independently of one another, hydrogen, alkyl, haloalkyl, aryl, alkoxy or hydroxyalkyl, with $R^4$ and $R^5$ preferably not both being hydrogen, or $R^4$ and $R^5$ form, together with the nitrogen atom to which they are bonded, a 5- or 6-membered heterocyclic ring;
where at least one of the substituents $R^1$, $R^4$ or $R^5$ is hydroxyalkyl, which comprises
reacting a mixture of an alkyne of the general formula II

where
$R^1$ has the abovementioned meanings,
a carbonyl compound of the general formula III

where
$R^2$ and $R^3$ have the abovementioned meanings,
and an amine of the general formula IV

where
$R^4$ and $R^5$ have the abovementioned meanings, with heterogeneous catalysis.

Halogen for the purpose of the present invention is fluorine, chlorine, bromine or iodine, in particular chlorine or bromine.

The term "alkyl" includes straight-chain and branched alkyl groups. These are preferably straight-chain or branched $C_1$–$C_{12}$-alkyl and, in particular, $C_1$–$C_6$-alkyl groups. Examples of alkyl groups are, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl and dodecyl.

Haloalkyl is an alkyl group as defined above, halogenated with one or more halogen atoms, in particular chlorine and bromine, partly or completely, preferably with one to three halogen atoms.

The above statements on the alkyl group and haloalkyl group apply correspondingly to the alkyl group in alkoxy, alkoxyalkyl and hydroxyalkyl radicals.

Cycloalkyl is preferably $C_3$–$C_8$-cycloalkyl such as cyclopropyl, cyclobutyl, cyclopentyl, cyclohexyl, cycloheptyl or cyclooctyl, or cyclopentylmethyl, cyclopentylethyl, cyclohexylmethyl and cyclohexylethyl.

Aryl is preferably phenyl or naphthyl.

The radicals $R^4$ and $R^5$ may form, together with the nitrogen atom to which they are bonded, a heterocyclic ring. Examples thereof are succinimido and phthalimido groups or an unsaturated or saturated 5- or 6-membered heterocyclic ring which may contain another hetero atom selected from S and N, preferably N. Examples which may be mentioned thereof are: piperidinyl, piperazinyl and tetrahydropyrimidinyl groups.

A preferred embodiment of the process according to the invention comprises the preparation of compounds where $R^1$ is a hydrogen, alkyl or $C_1$–$C_6$-hydroxyalkyl.

A preferred embodiment of the process according to the invention comprises the preparation of compounds where $R^2$ and $R^3$ in formula III are, independently of one another, hydrogen or alkyl. In particular, both $R^2$ and $R^3$ are hydrogen.

Another preferred embodiment of the process according to the invention comprises the preparation of compounds where $R^4$ and $R^5$ are, independently of one another, hydrogen, alkyl or $C_2$–$C_6$-hydroxyalkyl.

The heterogeneous catalysts which can be generally used for the process according to the invention are those also used for ethynylation reactions. Catalysts of these types are known in the art and are described, for example, in U.S. Pat. No. 4,119,790 and EP-A-80 794. In the process according to the invention there is preferably used a compound of a metal of the first or second subgroup of the periodic table on an inert carrier and, in particular, a supported copper acetylide catalyst which is prepared from a precursor which comprises 10 to 20% by weight of copper oxide, 1 to 5% by weight of bismuth oxide and silica as carrier material. A copper acetylide catalyst which is particularly preferably used has been prepared from a precursor which comprises about 14 to 15% by weight of CuO, about 4% by weight of $Bi_2O_3$ and about 80% of $SiO_2$.

The reaction can be carried out in the presence or absence of an inert organic solvent. The reaction rate can be increased and the yield possibly raised further by adding a dehydrating agent, e.g. sodium sulfate. The amount of dehydrating agent employed in this case is up to 1 mol per mole of carbonyl compound of the formula III.

The process according to the invention can be carried out in a stirred, tubular or loop reactor as continuous or batchwise process. The temperature for the reaction is generally from 40° to 150° C., preferably about 60° to 120° C.

The reaction is carried out under autogenous pressure with low-boiling substituted alkynes and amines and under atmospheric pressure with higher-boiling alkynes and amines.

If the compound of the formula II is acetylene, the carbonyl compound of the formula III and the amine of the formula IV are introduced together with the catalyst and, where appropriate, a solvent into an autoclave. Acetylene is injected until the pressure is about 3 to 7 bar, e.g. about 5 bar, and the autoclave is subsequently heated to the reaction temperature. Acetylene is then reinjected until the pressure is constant at about 15 to 25 bar, e.g. about 20 bar.

The following, non-limiting example is intended to illustrate the invention.

EXAMPLE 1

22.5 g (0.75 mol) of paraformaldehyde and 78.8 g (0.75 mol) of diethanolamine are introduced with 75 ml of THF into a 300 ml stirred autoclave. Then 12 g of activated copper acetylide catalyst (14–15% CuO, 4% $Bi_2O_3$, 80% $SiO_2$) are added to this solution. Subsequently, 5 bar of acetylene are injected and the solution is heated to 100° C. Acetylene is then reinjected until the pressure is constant at 20 bar. Workup by distillation allows 3-(di-2-hydroxyethylamino)propyne to be isolated in 85% yield.

As the example shows, the process according to the invention makes aminoalkynes of the general formula I available in surprisingly good yields in a reaction with heterogeneous catalysis.

EXAMPLE 2

112.12 g (2 mol) of 2-propyn-1-ol are mixed with 60 g of paraformaldehyde and 258.5 g (2 mol) of di-n-butylamine in a 500 ml three-neck flask. 20 g of activated copper acetylide catalyst (14–15% CuO, 4% $Bi_2O_3$, 80% $SiO_2$) are added to the solution. The mixture is then stirred at 90° C. for 12 hours. workup by distillation results in 4-(di-n-butylamino)-2-butyn-1-ol being isolated in 82% yield.

EXAMPLE 3

22.5 g (0.75 mol) of paraformaldehyde, 78.8 g (0.75 mol) of diethanolamine and 42 g (0.75 mol) of 1-propyn-3-ol are introduced with 150 ml of THF into a 500 ml three-neck flask. Then 12 g of activated copper acetylide catalyst (14–15% CuO, 4% $Bi_2O_3$, 80% $SiO_2$) are added to this solution. The solution is subsequently heated to 66° C. and stirred at this temperature for 12 hours. Workup by distillation allows 4-(di-2-hydroxyethylamino)-2-butyn-1-ol to be isolated in 85% yield.

We claim:

1. A process for preparing hydroxyalkyl-substituted aminoalkynes of the general formula I

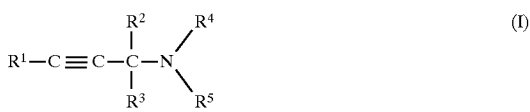

where $R^1$ is hydrogen, alkyl, haloalkyl, cycloalkyl, aryl, alkoxy, alkoxyalkyl or hydroxyalkyl;

$R^2$ and $R^3$ are, independently of one another, hydrogen, alkyl, haloalkyl, aryl or alkoxy;

$R^4$ and $R^5$ are, independently of one another, hydrogen, alkyl, haloalkyl, aryl, alkoxy or hydroxyalkyl, or $R^4$ and $R^5$ form, together with the nitrogen atom to which they are bonded, a 5- or 6-membered heterocyclic ring;

where at least one of the substituents $R^1$, $R^4$ or $R^5$ is hydroxyalkyl which comprises reacting a mixture of an alkyne of the general formula II

  (II)

where $R^1$ has the abovementioned meanings, a carbonyl compound of the general formula III

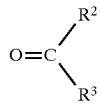  (III)

where $R^2$ and $R^3$ have the abovementioned meanings, and an amine of the general formula IV

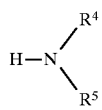  (IV)

where $R^4$ and $R^5$ have the abovementioned meanings, with heterogeneous catalysis.

2. The process as claimed in claim 1, wherein a compound of a metal of the first or second subgroup on an inert carrier is used as heterogeneous catalyst.

3. A process as claimed in claim 1, wherein a copper acetylide catalyst on a silica carrier doped with bismuth is used as heterogeneous catalyst.

4. A process as claimed in claim 1, wherein a dehydrating agent is added in the reaction in an amount of up to one mol per mole of carbonyl compound employed.

5. A process as claimed in claim 1, wherein the reaction is carried out continuously or batchwise in a stirred, tubular or loop reactor.

6. A process as claimed in claim 1, wherein a substituted alkyne is used as compound of the formula II, and the reaction is carried out under atmospheric pressure or the autogenous pressure of the reaction mixture.

7. A process as claimed in claim 1, wherein acetylene is used as compound of the formula II, and the reaction is carried out in an autoclave under an acetylene pressure of up to about 20 bar.

8. A process as claimed in claim 1, wherein the reaction is carried out at neutral or alkaline pH.

9. A process as claimed in claim 1, wherein the reaction takes place in nonaqueous medium.

10. A process as claimed in claim 1, wherein an alkyne of the formula II where $R^1$ is hydrogen, alkyl or alkoxyalkyl is reacted.

11. A process as claimed in claim 1, wherein a carbonyl compound of the formula III where $R^2$ and $R^3$ are, independently of one another, hydrogen or alkyl is reacted.

12. A process as claimed in claim 1, wherein a carbonyl compound of the formula III where $R^2$ and $R^3$ are each hydrogen is reacted.

13. A process as claimed in claim 1, wherein an amine of the formula IV where $R^4$ and $R^5$ are, independently of one another, hydrogen, alkyl or hydroxyalkyl is reacted.

14. A process as claimed in claim 1, wherein an amine of the formula IV where at least one of the radicals $R^4$ and $R^5$ is hydroxyalkyl is reacted.

* * * * *